United States Patent [19]

Deweerdt et al.

[11] Patent Number: 4,925,973
[45] Date of Patent: May 15, 1990

[54] PREPARATION OF DIESTERS OF HEXENEDIOIC ACID

[75] Inventors: Helene Deweerdt, Toulouse; Jean Jenck, Chassieu; Philippe Kalck, Castanet Tolosan, all of France

[73] Assignee: Rhone-Poulenc Chimie, Courbevoie, France

[21] Appl. No.: 365,768

[22] Filed: Jun. 13, 1989

[30] Foreign Application Priority Data

Jun. 13, 1988 [FR] France .................................. 88 08197

[51] Int. Cl.$^5$ ............................................. C07C 67/38
[52] U.S. Cl. .................................. 560/204; 560/190; 562/595
[58] Field of Search ................. 560/204, 190; 562/595

[56] References Cited

U.S. PATENT DOCUMENTS

| | | | |
|---|---|---|---|
| 3,367,961 | 2/1968 | Brewbaker | 560/207 |
| 4,060,547 | 11/1977 | Paulik et al. | 560/204 |
| 4,611,082 | 9/1986 | Chan et al. | 560/204 |

Primary Examiner—Werren B. Lone
Assistant Examiner—Vera C. Clarke
Attorney, Agent, or Firm—Burns, Doane, Swecker & Mathis

[57] ABSTRACT

Diesters of hexene-1,6-dioic acid are efficiently and selectively prepared by reacting carbon monoxide and an alcohol with at least one diacyloxylated butene compound, in the presence of (a) a catalytically effective amount of a palladium-based catalyst and (b) a quaternary onium chloride or bromide of nitrogen or phosphorus.

16 Claims, No Drawings

PREPARATION OF DIESTERS OF HEXENEDIOIC ACID

BACKGROUND OF THE INVENTION

1. Field of the Invention

The present invention relates to the preparation of diesters of hexene-1,6-dioic acid. These diesters can be hydrogenated to the corresponding diesters of adipic acid or adipates, which can in turn be hydrolyzed to produce adipic acid. (Adipic acid is one of the basic raw materials for nylon 66; for this reason alone, any novel process for the ultimate synthesis of such diacid and/or derivative thereof is of fundamental worth).

The present invention more especially relates to the preparation of diesters of 3-hexene-1,6-dioic acid by reacting carbon monoxide and an alcohol with at least one butene compound containing two acyloxy substituents in the presence of a catalyst based on palladium.

2. Description of the Prior Art

The preparation of a monoester of an alcohol and of a butenoic acid by reacting carbon monoxide and an alcohol with a monoester of an allyl alcohol, in the presence of a palladium-based catalyst, is described in U.S. Pat. No. 3,367,961. Ethyl vinylacetate can thus be prepared from allyl acetate, carbon monoxide and ethanol in the presence of palladium chloride and of palladium deposited on charcoal.

In U.S. Pat. No. 4,611,082 it is also indicated that the carbonylation of a solution of 1,4-diacetoxy-2-butene in a polar and nonbasic aprotic solvent selected from among the nitriles, bis(2-methoxy)-2-butene, bis(2-methoxyethyl) ether and methylene chloride, at 80° to 140° C. in the presence of a transition metal halide, is not observed in practice and that, in the presence of an alcohol, the rates increase and are comparable with those observed in the case of the carbonylation of 2-butene-1,4-diol. Concerning said latter substrate, it is also indicated that it does not enable satisfactory yields of linear carbonylation products to be expected under the aforementioned conditions and, in this context, substrates substituted by alkoxy groups in the 1,4-position are the preferred.

Moreover, 1,4-diacetoxy-2-butene is easily prepared by the acetoxylation of butadiene. It would, therefore, be highly desirable to provide this art with a process making it possible to produce, with a high efficiency, the diesters of 3-hexene-1,6-dioic acid from 1,4-diacetoxy-2-butene, for example, and, more generally, from butenes disubstituted by acyloxy groups.

SUMMARY OF THE INVENTION

Accordingly, a major object of the present invention is the provision of a novel process for the preparation of diesters of 3-hexenedioic acid by reacting carbon monoxide and an alcohol with at least one butene compound containing two acyloxy substituents, in the presence of a catalyst based on palladium, and characteristically wherein the reaction is also conducted in the presence of a quaternary onium halide of an element from Group VB of the Periodic Table selected from among nitrogen and phosphorus, said element being tetracoordinated to carbon atoms, with the proviso that the nitrogen may be coordinated to two pentavalent phosphorus atoms, and the halide anion is either the chloride or bromide.

DETAILED DESCRIPTION OF THE PREFERRED EMBODIMENTS OF THE INVENTION

More particularly according to the present invention, it has now surprisingly and unexpectedly been determined that the subject dicarbonylation reaction may be carried out under conditions of pressure and temperature which are acceptable on an industrial scale, with an appreciable selectivity for a linear dicarbonylated final product, with the proportions of monocarbonylated product and of branched dicarbonylated products being minimal.

The process according to the invention can be represented by the following reaction scheme, beginning with a 2-butene compound containing two acyloxy groups in the 1,4-positions:

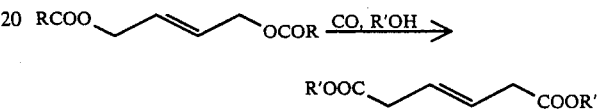

in which R is a linear or branched chain alkyl radical containing from 1 to 12 carbon atoms, optionally substituted by a phenyl group, or an aryl radical containing from 6 to 10 carbon atoms, optionally substituted by one or two alkyl radicals containing from 1 to 4 carbon atoms, with the proviso that such alkyl or aryl radicals may contain from 1 to 3 substituents selected from among fluorine and chlorine atoms and dialkylamino and N,N-dialkylamido radicals, the alkyl moieties of which containing not more than 4 carbon atoms; and R', which may be identical to or different from R, is a linear or branched chain alkyl radical containing from 1 to 12 carbon atoms, optionally substituted by a phenyl group, or an aryl radical containing from 6 to 10 carbon atoms, optionally substituted by one or two alkyl radicals containing from 1 to 4 carbon atoms, or a substituted such alkyl or aryl radical containing from 1 to 3 substituents selected from among fluorine, bromine and chlorine atoms.

The process according to the present invention requires the use of at least one butene compound disubstituted by acyloxy groups. By "acyloxy group" is intended a group of the formula RCOO- in which R is as defined above; "disubstituted butenes" are compounds of 2-butene which are substituted in positions 1 and 4 and compounds of 1-butene which are substituted in positions 3 and 4. Mixtures of 2-butene compounds disubstituted by different acyloxy groups; mixtures of 1-butene compounds disubstituted by different acyloxy groups; and mixtures of disubstituted 2-butene compounds and 1-butene compounds, can also be used as starting materials according to the present invention.

Indeed, it has now surprisingly been found that the selectivity of the subject process for a linear diester is substantially the same whether beginning with a 2-butene compound disubstituted by acyloxy groups in positions 1 and 4 or beginning with a 1-butene compound disubstituted by acyloxy groups in positions 3 and 4.

Exemplary of such butene compounds disubstituted by acyloxy groups are diacetoxybutenes, dipropionyloxybutenes, dibutyryloxybutenes and dibenzoyloxybutenes.

1,4-Diacetoxy-2-butene, 3,4-diacetoxy-1-butene, and mixtures thereof, are preferred starting materials according to the present invention.

The process according to the present invention also requires the use of an alcohol of formula R'OH, in which R' is as defined above.

Exemplary such alcohols are methanol, ethanol, isopropanol, n-propanol, tert-butanol, n-hexanol, 2-ethylhexanol, 1-nonanol, dodecanol, phenylethanol, phenol and trifluoroethanol.

An alkanol in which the radical R' contains at most 12 carbon atoms and preferably 4 carbon atoms is advantageously employed.

The amount of alkanol used according to this invention is not critical and may vary over wide limits.

To satisfactorily carry out the subject reaction, the molar ratio of alcohol to disubstituted butene will range from 1 to 100 and preferably from 1 to 50.

The process according to the present invention is conducted in the presence of a palladium-based catalyst.

Although the precise nature of the catalytically active species in the reaction under consideration has not been absolutely determined, it has been found that various palladium compounds and metallic palladium are useful precursors for carrying out the process of this invention.

Exemplary sources of palladium which can be used to carry out the process of the invention, the following are representative:
(i) metallic palladium deposited, if appropriate, onto a support such as charcoal, alumina or silica;
(ii) $PdCl_2$, $Pd(OAc)_2$;
(iii) palladium salts or $\pi$-allyl complexes, in which the anion coordinated to the Pd cation is selected from among the following anions: carboxylates such as the formate, acetate, propionate or benzoate, acetylacetonate, and halides such as $Cl^-$ and $Br^-$ and preferably $Cl^-$.

The precise amount of catalyst to be used, which may vary over wide limits, will primarily depend on a compromise between the desired efficiency and the catalyst cost and the other reaction conditions. In general, good results are obtained employing a substituted butene/palladium molar ratio of from 10 to 50. A ratio on the order of 200 can be used, the reaction being slower, and a ratio on the order of 2 or less, and such ratios present obstacles which are only economic in nature.

One of the critical features of the process of this invention is that the reaction is conducted in the added presence of a quaternary onium chloride (or bromide) of an element of Group VB of the Periodic Table that is either nitrogen or phosphorus, said element being tetracoordinated to carbon atoms, with the proviso, moreover, that the nitrogen may be coordinated to two pentavalent phosphorus atoms.

By "quaternary onium cation in which the element of Group VB is tetracoordinated to carbon atoms" are intended cations formed from nitrogen or phosphorus and from four identical or different monovalent hydrocarbon groups, in which the free valency is borne by a carbon atom, each group being bonded to the above-mentioned element via such free valency, with the proviso that any two of these groups may together form a simple divalent radical.

To satisfactorily carry out the process of the invention, the quaternary onium salt advantageously has a quaternary onium cation corresponding to one of the formulae (I) to (IV) below:

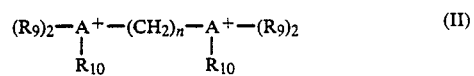

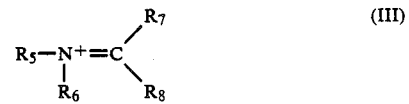

in which A is nitrogen or phosphorus; $R_1$, $R_2$, $R_3$ and $R_4$, which may be identical or different, are each a linear or branched chain alkyl radical containing from 1 to 16 carbon atoms, optionally substituted by a phenyl, hydroxyl, halo, nitro, alkoxy or alkoxycarbonyl group, a linear or branched chain alkenyl radical containing from 2 to 12 carbon atoms, preferably from 4 to 8 carbon atoms, an aryl radical containing from 6 to 10 carbon atoms, optionally substituted by one or more alkyl radicals containing from 1 to 4 carbon atoms, or alkoxy, alkoxycarbonyl or halo radicals, with the proviso that two of such radicals $R_1$ to $R_4$ may together form a single linear or branched chain alkylene, alkenylene or alkadienylene radical containing from 3 to 6 carbon atoms; $R_5$, $R_6$, $R_7$ and $R_8$, which may be identical or different, are each a linear or branched chain alkyl radical containing from 1 to 4 carbon atoms, with the provisos that the radicals $R_7$ and $R_8$ may together form a single alkylene radical containing from 3 to 6 carbon atoms, and that the radicals $R_6$ and $R_7$ or $R_6$ and $R_8$ may together form a single alkylene, alkenylene or alkadienylene radical containing 4 carbon atoms and forming a nitrogenous heterocyclic ring with N; $R_9$ is a linear or branched chain alkyl radical containing from 1 to 4 carbon atoms or a phenyl radical; $R_{10}$ is a linear or branched chain alkyl radical containing from 1 to 4 carbon atoms, identical to or different from $R_9$, or a linear or branched chain alkenyl radical containing from 2 to 12 carbon atoms, preferably from 4 to 8 carbon atoms; D is an integer greater than or equal to 1 and less than or equal to 10 and preferably less than or equal to 6; and $R_{11}$ is an aryl radical containing from 6 to 10 carbon atoms, optionally substituted by one or more alkyl groups containing from 1 to 4 carbon atoms, or alkoxy, alkoxycarbonyl or halo groups.

Exemplary of the quaternary onium cations corresponding to formula (I), the following are representative:
tetramethylammonium
triethylmethylammonium
tributylmethylammonium
trimethyl(n-propyl)ammonium
tetraethylammonium
tetrabutylammonium
dodecyltrimethylammonium
methyltrioctylammonium
heptyltributylammonium
tetrapropylammonium
tetrapentylammonium
tetrahexylammonium
tetraheptylammonium
tetraoctylammonium tetradecylammonium
butyltripropylammonium
methyltributylammonium
pentyltributylammonium
methyldiethylpropylammonium
ethyldimethylpropylammonium
tetradodecylammonium
tetraoctadecylammonium
hexadecyltrimethylammonium
benzyltrimethylammonium
benzyldimethylpropylammonium
benzyldimethyloctylammonium
benzyltributylammonium
benzyltriethylammonium
phenyltrimethylammonium
benzyldimethyltetradecylammonium
benzyldimethylhexadecylammonium
dimethyldiphenylammonium
methyltriphenylammonium
buten-2-yltriethylammonium
N,N-dimethyltetramethyleneammonium
N,N-diethyltetramethyleneammonium
tetramethylphosphonium
tetrabutylphosphonium
ethyltrimethylphosphonium
trimethylpentylphosphonium
octyltrimethylphosphonium
dodecyltrimethylphosphonium
trimethylphenylphosphonium
diethyldimethylphosphonium
dicyclohexyldimethylphosphonium
dimethyldiphenylphosphonium
cyclohexyltrimethylphosphonium
triethylmethylphosphonium
methyltri(isopropyl)phosphonium
methyltri(n-propyl)phosphonium
methyltri(n-butyl)phosphonium
methyltri(2-methylpropyl)phosphonium
methyltricyclohexylphosphonium
methyltriphenylphosphonium
methyltribenzylphosphonium
methyltri(4-methylphenyl)phosphonium
methyltrixylylphosphonium
diethylmethylphenylphosphonium
dibenzylmethylphenylphosphonium
ethyltriphenylphosphonium
tetraethylphosphonium
ethyltri(n-propyl)phosphonium
triethylpentylphosphonium
hexadecyltributylphosphonium
ethyltriphenylphosphonium
n-butyltri(n-propyl)phosphonium
butyltriphenylphosphonium
benzyltriphenylphosphonium
($\beta$-phenylethyl)dimethylphenylphosphonium
tetraphenylphosphonium
triphenyl(4-methylphenyl)phosphonium
tetrakis(hydroxymethyl)phosphonium
tetrakis(2-hydroxyethyl)phosphonium.

Exemplary of the cations corresponding to formula (II), the following are representative:
N-methylpyridinium
N-ethylpyridinium
N-hexadecylpyridinium
N-methylpicolinium.

Exemplary of cations corresponding to formula (III), the following are representative:
1,2-bis(trimethylammonium)ethane
1,3-bis(trimethylammonium)propane
1,4-bis(trimethylammonium)butane
1,3-bis(trimethylammonium)butane.

Exemplary of the cations corresponding to formula (IV), the following are representative:
bis(triphenylphosphine)iminium
bis(tritolylphosphine)iminium.

One or more quaternary onium chloride(s) is (are) preferably used.

The onium cations which advantageously are used are those corresponding to the above formula (I) in which A is phosphorus, and $R_1$, $R_2$, $R_3$ and $R_4$, which may be identical or different, are each a linear or branched chain alkyl radical containing from 1 to 8 carbon atoms, or a phenyl or 4-methylphenyl radical.

A tetraalkylphosphonium chloride is preferably employed.

Tetrabutylphosphonium chloride is commercially available and particularly effective. Thus, it is especially preferred.

It has also been found that the beneficial effect contributed by the presence in the carbonylation medium of a quaternary onium salt as defined above is perceptible starting with an onium cation/palladium molar ratio of 0.5; however, a particularly advantageous effect has been found when said ratio ranges from 1 to 50, although a higher ratio is not detrimental to the reaction.

Also for satisfactorily carrying out the carbonylation reaction according to this invention, it is preferable, when selecting the onium cation/palladium ratio, to take account of the palladium concentration in the mixture and especially of the disubstituted butene/palladium molar ratio. Thus, the higher the disubstituted butene/palladium ratio, the more advantageous it is to employ a high onium cation/palladium ratio.

The reaction can generally be conducted in liquid phase at a temperature of from 50° to 150° C., preferably from 80° to 130° C., under a carbon monoxide pressure of from 20 to 250 bar and preferably from 90 to 180 bar. Inert gases, such as nitrogen, argon or carbon dioxide, may be present together with the carbon monoxide.

The reaction can, of course, be conducted in the presence of solvents or diluents which are exogenous to the reaction mixture, such as aromatic hydrocarbons, ketones, nitriles, esters, or amides of carboxylic acids.

When the reaction is complete or the intended reaction time has elapsed, the desired diester is recovered by any appropriate means, for example by distillation.

In order to further illustrate the present invention and the advantages thereof, the following specific examples are given, it being understood that same are intended only as illustrative and in nowise limitative. In said examples to follow, the yields are expressed in relation to the diacetoxybutene charged.

EXAMPLE 1

The following materials were introduced into an autoclave made of Hastelloy B2:
30 cm³ (740 mmol) of methanol, 23 mmol of 1,4-diacetoxy-2-butene, 1.25 mmol of PdCl₂ and 5.0 g (17 mmol) of tetrabutylphosphonium chloride. The reaction mixture was maintained at 100° C. for 21 hours, under stirring, at a constant pressure of 165 bar, and with a pure carbon monoxide feed.

Analysis by gas phase chromatography, using the internal reference quantitative technique, made it possible to ascertain:

(a) a complete degree of conversion of diacetoxybutene;
(b) a 65% yield of dimethyl 3-hexenedioate.

EXAMPLE 2

The procedure of Example 1 was repeated, but with the total pressure reduced to 100 bar and the time to 6 hours. 95% of the substrate was converted, with a methyl 3-hexenedioate yield equal to 43%.

EXAMPLE 3

The procedure of Example 2 was repeated, but the methanol was replaced with a mixture of 10 cm³ of methanol and 20 cm³ of acetonitrile. Over 6 hours, 98% of the diacetoxybutene was converted, with an 84% yield of methyl 3-hexenedioate.

EXAMPLE 4

1,4-Diacetoxy-2-butene was isomerized to 3,4-diacetoxybutene by heating to 100° C. under a nitrogen atmosphere in a glass ampoule in the presence of $H_2PtCl_6$ (approximately 3% by weight).

After removal of the platinum on kieselguhr, the mixture of isomers (2/1 linear/branched) was subjected to a carbonylation under the conditions of Example 1. It was found that both isomers of diacetoxybutene were converted into linear diester.

EXAMPLE 5

The procedure of Example 3 was repeated, but the acetonitrile was replaced with the same volume of methyl isobutyl ketone.

Over 6 hours, 92.5% of the diacetoxybutene was converted, with an 80% yield of methyl 3-hexenedioate.

EXAMPLE 6

The procedure of Example 3 was repeated, but using 10 cm³ of 1-nonanol instead of methanol. The formation of dinonyl 3-hexenedioate and of nonyl acetoxypentenoate was observed.

EXAMPLE 7

The procedure of Example 3 was repeated, but the acetonitrile was replaced with the same volume of toluene.

Over 6 hours, 91% of the diacetoxybutene was converted, with an 82% yield of methyl 3-hexenedioate.

EXAMPLE 8

Example 7 was repeated at 60° C.

Over 6 hours, 60% of the diacetoxybutene was converted, with a 55% yield of methyl 3-hexenedioate.

EXAMPLE 9

Example 7 was repeated at 140° C.

Over 6 hours, 92% of the diacetoxybutene was converted, with an 85% yield of methyl 3-hexenedioate.

EXAMPLE 10

Example 7 was repeated, using only one mmol of tetrabutylphosphonium chloride.

Over 6 hours, 89% of the diacetoxybutene was converted, with a 13% yield of methyl 3-hexenedioate.

CONTROL TEST (a):

Example 7 was repeated, but the tetrabutylphosphonium chloride was omitted.

Over 6 hours, 85% of the diacetoxybutene was converted, with a 5% yield of methyl 3-hexenedioate.

EXAMPLE 11

Example 7 was repeated, with the tetrabutylphosphonium chloride being replaced with 17 mmol of tetramethylammonium chloride.

Over 6 hours, 70% of the diacetoxybutene was converted, with a 70% yield of methyl 3-hexenedioate.

EXAMPLE 12

Example 11 was repeated, but the tetrabutylammonium chloride was replaced with tetramethylphosphonium chloride.

Over 6 hours, 70% of the diacetoxybutene was converted, with a 51% yield of methyl 3-hexenedioate.

EXAMPLE 13

In the autoclave and according to the operating procedure described in Example 1, a test was carried out on a charge containing:
(i) 10 cm³ of methanol;
(ii) 20 cm³ of toluene;
(iii) 23 mmol of 1,4-diacetoxy-2-butene;
(iv) 17 mmol of tetrabutylphosphonium chloride; and
(v) 1 mmol of palladium, introduced in the form of palladium deposited onto carbon black (at a concentration of 5% of palladium).

Over 6 hours, at 100° C., at a constant pressure of 100 bar and with a pure carbon monoxide feed, 98% of the diacetoxybutene was converted, with a 58% yield of methyl 3-hexenedioate.

EXAMPLE 14

The procedure of Example 3 was repeated, but the acetonitrile was replaced with the same volume of ethyl acetate, and methanol with the same volume of ethanol.

Over 6 hours, 87% of the diacetoxybutene was converted, with an 83% yield of 3-hexenedioate.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparatron of a diester of 3-hexenedioic acid, comprising reacting carbon monoxide and an alcohol with at least one butene compound disubstituted by acyloxy groups, in the presence of (a) a catalytically effective amount of a palladium-based catalyst, and (b) a quaternary onium halide of nitrogen or phosphorus, said nitrogen or phosphorus being tetracoordinated to carbon atoms, with the proviso that the nitrogen may be coordinated to two pentavalent phosphorus atoms, and wherein the halide anion is the chloride or bromide.

2. The process as defined by claim 1, said quaternary onium halide comprising a quaternary onium cation corresponding to one of the following formulae (I) to (IV):

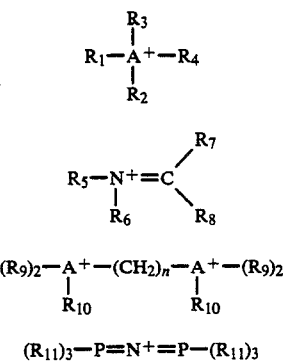

in which A is nitrogen or phosphorus; $R_1$, $R_2$, $R_3$ and $R_4$, which may be identical or different, are each a linear or branched chain alkyl radical containing from 1 to 16 carbon atoms, optionally substituted by a phenyl, hydroxyl, halo, nitro, alkoxy or alkoxycarbonyl group, a linear or branched chain alkenyl radical containing from 2 to 12 carbon atoms, an aryl radical containing from 6 to 10 carbon atoms, optionally substituted by one or more alkyl radicals containing from 1 to 4 carbon atoms, or alkoxy, alkoxycarbonyl or halo radicals, with the proviso that two of such radicals $R_1$ to $R_4$ may together form a linear or branched chain alkylene, alkenylene or alkadienylene radical containing from 3 to 6 carbon atoms; $R_5$, $R_6$, $R_7$ and $R_8$, which may be identical or different, are each a linear or branched chain alkyl radical containing from 1 to 4 carbon atoms, with the provisos that the radicals $R_7$ and $R_8$ may together form a single alkylene radical containing from 3 to 6 carbon atoms, and that the radicals $R_6$ and $R_7$ or $R_6$ and $R_8$ may together form a single alkylene, alkenylene or alkadienylene radical containing 4 carbon atoms and forming a nitrogenous heterocyclic ring with N; $R_9$ is a linear or branched chain alkyl radical containing from 1 to 4 carbon atoms or a phenyl radical; $R_{10}$ is a linear or branched chain alkyl radical containing from 1 to 4 carbon atoms, identical to or different from $R_9$; or a linear or branched chain alkenyl radical containing from 2 to 12 carbon atoms; n is an integer greater than or equal to 1 and less than or equal to 10; and $R_{11}$ is an aryl radical containing from 6 to 10 carbon atoms, optionally substituted by one or more alkyl groups containing from 1 to 4 carbon atoms, or alkoxy, alkoxycarbonyl or halo groups.

3. The process as defined by claim 1, said quaternary onium halide is a chloride.

4. The process as defined by claim 2, said quaternary onium cation corresponding to the formula (I), in which A is phosphorus; and $R_1$, $R_2$, $R_3$ and $R_4$, which may be identical or different, are each a linear or branched chain alkyl radical containing from 1 to 8 carbon atoms, or a phenyl or 4-methylphenyl radical.

5. The process as defined by claim 1, said quaternary onium halide is tetrabutylphosphonium chloride.

6. The process as defined by claim 1, wherein the molar ratio of the onium cation to palladium ranges from 1 to 50.

7. The process as defined by claim 1, wherein the molar ratio of the disubstituted butene to palladium ranges from 2 to 200.

8. The process as defined by claim 1, wherein the molar ratio of the alcohol to the disubstituted butene ranges from 1 to 100.

9. The process as defined by claim 1, carried out at a temperature of from 50 to 150° C.

10. The process as defined by claim 1, carried out at a pressure of from 20 to 250 bar.

11. The process as defined by claim 1, said disubstituted butene is 1,4-diacetoxy-2-butene, 3,4-diacetoxy-1-butene, or mixture thereof.

12. The process as defined by claim 7, said molar ratio ranging from 10 to 50.

13. The process as defined by claim 8, said molar ratio ranging from 1 to 50.

14. The process as defined by claim 9, said temperature ranging from 80° to 130° C.

15. The process as defined by claim 10, said pressure ranging from 90 to 180 bar.

16. The process as defined by claim 1, said alcohol is methanol, ethanol, isopropanol, n-propanol, tert-butanol, n-hexanol, 2-ethylhexanol, 1-nonanol, dodecanol, phenylethanol, phenol, or trifluoroethanol.

* * * * *